US00PP23315P2

(12) United States Plant Patent
Cain

(10) Patent No.: US PP23,315 P2
(45) Date of Patent: Jan. 8, 2013

(54) GRAPEVINE 'IFG EIGHT'

(50) Latin Name: *Vitis vinifera*
Varietal Denomination: IFG Eight

(75) Inventor: David Cain, Bakersfield, CA (US)

(73) Assignee: International Fruit Genetics LLC, Bakersfield, CA (US)

( * ) Notice: Subject to any disclaimer, the term of this patent is extended or adjusted under 35 U.S.C. 154(b) by 0 days.

(21) Appl. No.: 13/134,946

(22) Filed: Jun. 22, 2011

(51) Int. Cl.
*A01H 5/00* (2006.01)

(52) U.S. Cl. ..... Plt./205

(58) Field of Classification Search ..... Plt./205
See application file for complete search history.

*Primary Examiner* — Annette Para

(57) ABSTRACT

This invention is a new and distinct grapevine variety denominated 'IFG Eight'. The new grapevine is characterized by producing crisp oval, seedless fruits which are fully black in color and ripen early in the growing season.

1 Drawing Sheet

Latin name of the genus and species claimed: *Vitis vinifera*. Variety denomination: 'IFG Eight'.

BACKGROUND OF THE INVENTION

The new and distinct grapevine described and claimed herein originated from a hand pollination of the Summer Royal (non-patented) variety and the Regal variety (South African PBR ZA971795) performed in May 2004. The resulting plants were planted into the field in April 2005. The present variety of grapevine was selected as a single plant in August 2006 and was first asexually propagated by hardwood cuttings in December 2006. The resulting propagules were planted during April 2007 near Delano, Kern County Calif. and were found to reproduce true-to-type through at least two generations of asexual propagation.

BREIF SUMMARY OF THE INVENTION

The new grapevine 'IFG Eight' is characterized by producing naturally large, oval, completely black seedless berries which are firm in texture and ripen early in the growing season. Fruits normally ripen in late July to early August near Delano, Calif.

To the inventor's knowledge, the known variety which the new grapevine variety is most similar to is its parent the Summer Royal variety. 'IFG Eight' can be distinguished from the Summer Royal variety by its producing naturally larger berries (about 8.4 grams as opposed to about 5.0 grams for Summer Royal), by having a broader, more desirable cluster shape and thicker and tougher peduncle and pedicle. The 'IFG Eight' stores better than the Summer Royal variety. 'IFG Eight' exhibits very little stem drying, berry shatter or decay when stored for up to eight weeks.

The 'IFG Eight' differs from the Regal variety by producing oval black colored fruits as opposed to the elongated white fruits of the Regal variety.

BRIEF DESCRIPTION OF THE FIGURE

The accompanying photographic illustration in FIG. 1 illustrates in full color 'IFG Eight'. The colors are as nearly true as is reasonably possible in a color representation of this type.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published by The Royal Horticultural Society, London, England.

Throughout this specification subjective description values conform to those set forth by the International Plant Genetic Resources Institute publication 'Descriptors for Grape' (*Vitis* spp.) (1983) which was developed in collaboration with the Office International de la Vigne et du Vin (OIV) and the International Union for the Protection of New Varieties of Plants (UPOV).

The descriptive matter which follows pertains to 'IFG Eight' plants grown in the vicinity of Delano, Kern County, Calif. during 2010, and is believed to apply to plants of the variety grown under similar conditions of soil and climate elsewhere:

Vine:

*General*.—Size — Medium. Vigor — Vigorous. Density of foliage — Dense. Productivity — Moderately Productive. Root stock — Own root. Training method — Typically spur pruned leaving 2 bud spurs but may require cane pruning under some climatic and cultural conditions.

*Trunk*.—Trunk diameter of 4-year-old vines at 30 cm above the soil line — 5.9 cm. Shape — Medium. Straps — Short-Split. Surface texture — Medium-Shaggy. Inner bark color — 164B, 165B, C, 166A.

Shoots:

*Young shoot*.—Form of tip — Fully opened. Distribution of anthocyanin coloration of tip — Absent. Intensity of anthocyanin coloration of tip — Absent. Density of prostrate hairs of tip — Medium. Density of erect hairs of tip — Absent. Color — 146C, D, 144A.

*Woody shoots* (*mature canes*).—Shape — Medium. Internode length — Medium; About 13.0 cm. Width at node — About 1.6 cm. Cross section — Circular. Surface — Striate. Main color — Reddish brown; 177C, D, 174B,C. Density of erect hairs of nodes —

None. Density of erect hairs on internodes — None. Growth of axillary shoots at full bloom — Medium-Strong. Approximately 11.1 cm.

*Flowering shoot*.—Vigor during flowering — Medium-Strong. Attitude during flowering on shoots not tied — Semi-erect to Semi-drooping. Color — dorsal side of internodes — Yellow green with Red stripes; 145A, 146A, B, 144A. Color — ventral side of internodes — Green. Color — dorsal side of nodes — Green-greyed purple; 183A, B. Color — ventral side of nodes — Green. Density of prostrate hairs of nodes — Very sparse. Density of erect hairs of nodes — None. Density of prostrate hairs on internode — Very sparse. Density of erect hairs on internode — None. Anthocyanin coloration of buds — Absent.

*Tendrils*.—Distribution on the shoot (at full flowering) — Discontinuous. Length of Tendril — Medium-Long; About 20.4 cm. Thickness — Medium. Color — 144C, 151A. Form — bifurcated. Number of consecutive tendrils — 2.

Leaves:

*Young leaves*.—Color of upper surface of first four distal unfolded leaves — Green. Average intensity of anthocyanin coloration of six distal leaves prior to flowering — Weak. Density of prostrate hairs between veins (lower surface) — Very sparse. Density of prostrate hairs on veins (lower surface) — Sparse-Medium. Density of erect hairs between veins (lower surface) — Absent. Density of erect hairs on veins (lower surface) — Very sparse.

*Mature leaves*.—Average length — About 13.7 cm. Average width — About 14.9 cm. Mature leaf size — Medium. Shape of blade — Pentagonal. Number of lobes — 5. Anthocyanin coloration of main veins on upper side of blade — Absent. Mature leaf profile — Flat. Blistering surface of blade upper surface — Very weak. Leaf blade tip — In the plane of the leaf. Undulation of margin — Slight. Thickness — Medium. Undulation of blade between main and lateral veins — Only near petiole. Shape of teeth — Mixture of both side's straight and both sides convex. Length of teeth — Medium. Ratio length/width of teeth — Medium. Shape of upper lateral sinuses — Lobes slightly overlapping. Depth of upper lateral sinuses — Medium. General shape petiole sinus — Slightly open. Shape of base of upper leaf sinuses — V-shaped. Tooth at petiole sinus — Absent. Density of prostrate hairs between veins on lower surface of blade — Absent. Density of erect hairs between veins on lower surface of blade — Absent. Density of prostrate hairs on main veins on lower surface of blade — Sparse. Density of erect hairs on main veins on lower surface of blade — None or very sparse. Density of prostrate hairs on main veins on upper surface of blade — Sparse. Density of erect hairs on main veins on upper surface of blade — Very sparse. Autumn coloration of leaves — Yellow-green; 151A, Grey-yellow; 160A, Grey-red; 178C, Grey-purple; 187A, B, 186C.

*Upper surface*.—Color — 137A, 144A, 146A, B. Anthocyanin coloration of main veins — Absent to Very weak. Surface appearance — Dull. Blistering surface of blade — Weak.

*Lower surface*.—Color — 147B, 144A. Anthocyanin coloration of main veins (lower surface) — Absent. Glossiness — Weak. Surface texture — Smooth. Surface appearance — Semi-glossy to Dull.

*Petiole*.—Length — About 10.5 cm. Length of petiole compared to middle vein — Slightly shorter. Density of prostrate hairs on petiole — None. Density of erect hairs on petiole — None.

*Buds*.—Bud fruitfulness — Basal: Mostly fruitful. Position of first fruitful shoot on previous season cane — $1^{st}$ to $2^{nd}$ node. Time of bud burst — Early to Medium, Feb. 25, 2010.

Flowers:

*General*.—Flower sex — Hermaphrodite. Length of first inflorescence — Medium; About 19.7 cm long by 12.8 cm wide. Position of first flowering and fruiting node — $2^{nd}$-$3^{rd}$ (current season growth). Number of inflorescence per flowering shoot — 1. Time of bloom — Early as compared with similar varieties in the growing area of Delano, Calif. Date of full bloom — May 15, 2010.

Fruit:

*General*.—Ripening period — Early; Approximately Aug. 9, 2010. Use — Fresh market. Keeping quality — Good. Resistance to — insects: Average typical of *Vitis vinifera* species. Diseases: Average typical of *Vitis vinifera* species. Refractometer test — solid-sugar: About 18.6 Brix. Brix/acid — About 37.2. Titratable acidity — About 0.50. Juice pH — About 3.7.

*Cluster*.—Mature cluster length (peduncle excluded) — About 23.2 cm. Mature cluster width — About 19.3 cm. Mature cluster weight — About 1154 g. Bunch density — Medium. Number of berries — About 198. Form — Conical.

*Peduncle*.—Lignification of peduncle — Medium. Length of peduncle — Long. Approximately 6.5 cm.

*Berry*.—Uniformity of size — Uniform. Single berry weight — About 8.4 g natural; to about 9.1 g when treated with gibberellic acid. Shape — Obtuse ovate. Seeds — Traces occasionally noticeable. Cross section — Circular. Berry dimensions — longitudinal axis: About 30.6 mm. horizontal axis: About 21.3 mm. Berry firmness — Medium firm. Particular flavor — Neutral. Bloom (cuticular wax) — Weak to Medium. Berry separation from pedicel — Medium difficult. Skin color (without bloom) — Greyed-Purple; N186A, C, 187A.

*Skin*.—Thickness — Medium. Texture — Medium. Reticulation — Absent. Tenacity — Tenacious to flesh.

What is claimed:

1. A new and distinct variety of grapevine as herein illustrated and described.

* * * * *

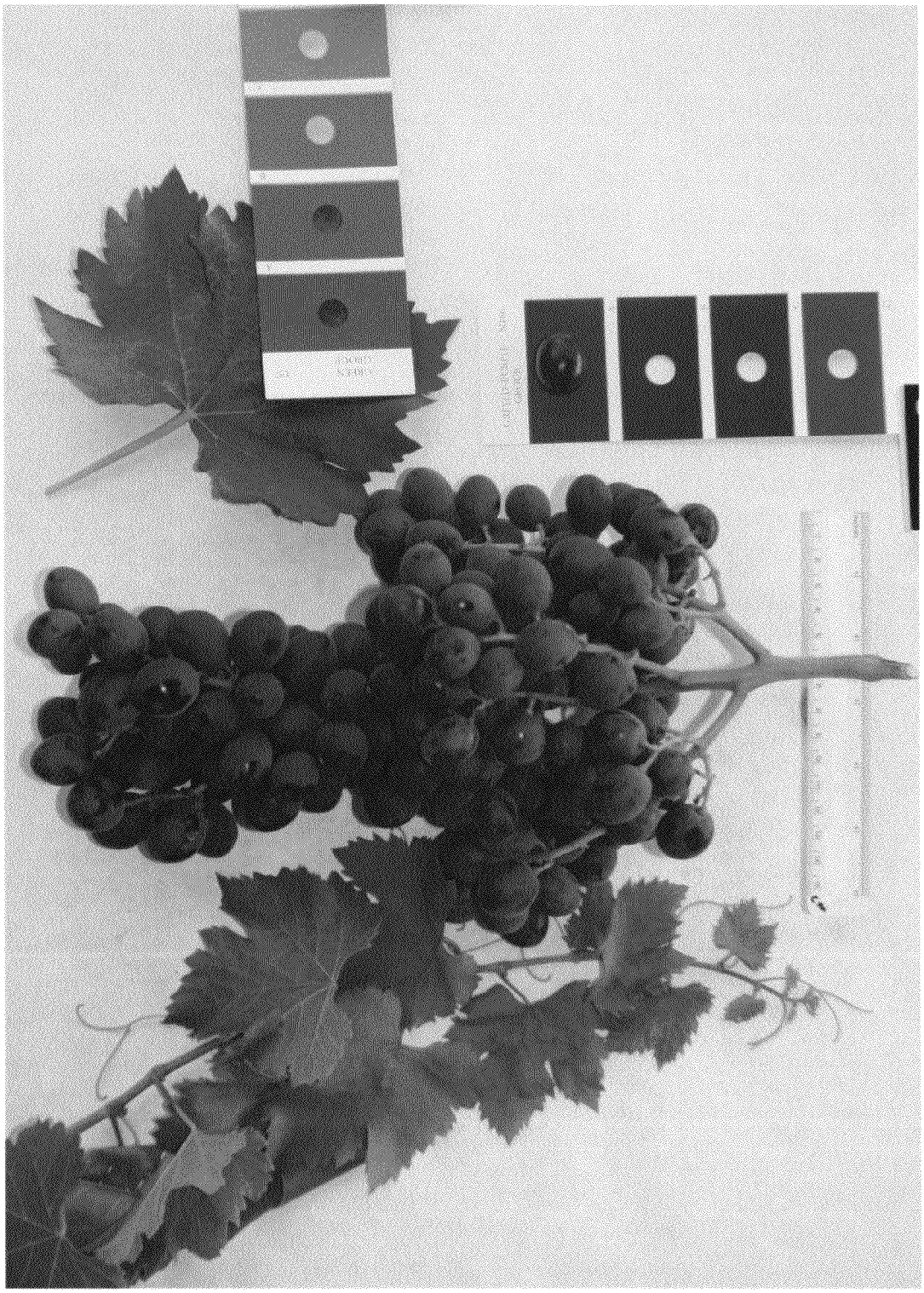
COLOR CHART
Green
Yellow
Orange
Red
Purple
Blue
Black
Brown
Gray
White
Yellow
Orange
Red
Purple
Blue
Black
Brown
Gray
White
Green